United States Patent
Li et al.

(10) Patent No.: US 8,298,245 B2
(45) Date of Patent: Oct. 30, 2012

(54) THREE-DIMENSIONAL POSITIONING DEVICE FOR MINIMALLY INVASIVE SURGERY

(75) Inventors: Shih-Tseng Li, Taipei (TW); Yau-Zen Chang, Gueishan Township, Taoyuan County (TW); Heng-Liang Liu, Pingtung (TW); Shun-Chung Chuang, Changhua (TW)

(73) Assignee: Chang Gung University, Taoyuan County (TW)

( * ) Notice: Subject to any disclaimer, the term of this patent is extended or adjusted under 35 U.S.C. 154(b) by 515 days.

(21) Appl. No.: 12/541,997

(22) Filed: Aug. 17, 2009

(65) Prior Publication Data

US 2011/0040304 A1    Feb. 17, 2011

(51) Int. Cl.
*A61B 19/00* (2006.01)
(52) U.S. Cl. ......... 606/130; 600/424; 600/427; 600/429
(58) Field of Classification Search .................... 606/54, 606/56, 130; 267/154–157
See application file for complete search history.

(56) References Cited

U.S. PATENT DOCUMENTS

| | | | | |
|---|---|---|---|---|
| 2,697,433 | A * | 12/1954 | Zehnder | 606/96 |
| 5,618,288 | A * | 4/1997 | Calvo | 606/130 |
| 6,331,180 | B1 * | 12/2001 | Cosman et al. | 606/130 |
| 6,413,263 | B1 * | 7/2002 | Lobdill et al. | 606/129 |
| 7,231,723 | B1 * | 6/2007 | O'Neill et al. | 33/512 |

* cited by examiner

*Primary Examiner* — Gary Jackson
*Assistant Examiner* — Kendra Obu

(57) ABSTRACT

A three-dimensional positioning device for minimally invasive surgery includes a base, two angle adjustable assemblies, an arc, a sliding assembly, a first positioning assembly, a second positioning assembly and a third positioning assembly. The base includes two first frames and two second frames. Two ends of each second frame are connected to the first frames respectively. Each first frame has a pivotal member. The angle adjustable assemblies are pivotably connected to the pivotal member of the first frame respectively. The arc includes a hollow track member. The angle adjustable assemblies are connected to two ends of the arc. The sliding assembly is mounted on the track member of the arc according to a predetermined position of a nidus. Therefore, the three-dimensional positioning device can effectively improve precision and operation more precisely in minimally invasive surgery to increase surgery success rate.

10 Claims, 12 Drawing Sheets

THREE-DIMENSIONAL POSITIONING DEVICE FOR MINIMALLY INVASIVE SURGERY

BACKGROUND OF THE INVENTION

1. Field of Invention

The invention relates to a positioning device for minimally invasive surgery and, more particularly, to a three-dimensional positioning device for minimally invasive neurosurgery.

2. Description of Related Art

In recent years, a medical operation method has developed toward minimally invasive surgery. Minimally invasive surgery is characterized in a small incision, such as skull tumor electro-burning surgery, nail spine implant surgery, or artificial dental implant surgery. It has several advantages such as a small incision, short healing time, low probability to infect and less blood loss. The smaller incision is difficult to invade and is difficult to mount an instrument or implant. Thus, it is necessary to have a better and precise positioning device to increase the surgery success rate.

Take the skull tumor electro-burning surgery for an example. Common brain diseases are inclusive of brain tumors, Parkinson's disease, epilepsy, etc. These diseases may cause patients to have several symptoms such as trembling, headache, vomiting, dysopia or unconsciousness. These symptoms can result in lowering the quality of life by a wide margin. Seriously, these diseases may endanger the life of the patient. Furthermore, if conservative therapy can't improve the health of the patient, it is necessary to utilize invasive surgery to treat these diseases.

Conventionally, the surgeon has to diagnose the position of the nidus by computerized tomography (CT scan) and clinical experience. Then, the surgeon utilizes a cauterizing needle and a frame to mount on the skull of the patient for reaching the position of the nidus and to get rid of the nidus.

Recently, computer technology has developed and advanced well. A three-dimensional image and auxiliary positioning system has developed to assist the operation of the invasive surgery. Conventional procedures of computer-assisted skull surgery are described as follows. The patient has to be mounted on a rectangular frame to execute a brain CT scan before surgery. After image processing in the computer, the three-dimensional relative position among the rectangular frame, the skull and the nidus is obtained. Surgeons have to plan the invasive path and depth of the cauterizing needle by utilizing the computer to calculate the rotation angle or displacement of each movable element in the mechanism when the rectangular frame mounts on the patient. Until in the surgery, surgeons utilize the rectangular frame, an optical ball device and a camera to take a picture. Surgeons also can utilize LEDs to emit signals and to co-operate with a receiver to obtain the position of the rectangular frame. At the same time, the position of the skull 110 and the position of the nidus can also be obtained. Then, a positioning device is moved onto the rectangular frame mounted on the patient. Finally, as shown in FIG. 12, the cauterizing needle is mounted, and the cauterizing needle is utilized to invade to the nidus for treating.

Besides, another conventional three-dimensional positioning device utilizes a rectangular frame and a semicircular frame to position. Such conventional three-dimensional positioning device in use has to cover the whole skull. It reduces the operating space for the surgeons. Furthermore, it is without the design of the cauterizing needle adjustment mechanism. It results in surgeons having to operate the cauterizing needle manually. Therefore, the invasive depth and invasive speed can't be accurately controlled.

In addition, another conventional three-dimensional positioning device utilizes a link mechanism to make the cauterizing needle be movable or fixed. Such three-dimensional positioning device can provide a wider movable range for the cauterizing needle. However, it also leads to a problem of cumbersome volume. It reduces the operating space for the surgeons. It also leads to a poor rigidity due to the link mechanism.

Besides, another conventional three-dimensional positioning device utilizes an upper member and a lower member to rotate. The upper member is semicircular. The upper member can provide a curve movement. Such conventional three-dimensional positioning device is small and can be directly mounted on the incision of the skull. It utilizes a rotatable knob to adjust the cauterizing needle into the nidus with a small extent. However, due to the small volume, it leads to a smaller scale. Smaller scale may lead to difficult adjustment in practical operation. At the same time, such conventional three-dimensional positioning device has many parts. It is time-consuming to assemble the conventional three-dimensional positioning device.

To summarize, conventional three-dimensional positioning devices have many problems such as low precision, poor rigidity, and so on. Furthermore, as shown in FIG. 12, the conventional three-dimensional positioning device 100 has many directions D to adjust. It results in many problems such as a complex structure, difficult operation procedures and low precision. Due to the complex structure, difficult operation procedures and low precision, it may result in a longer operation time to decrease the surgery success rate. Seriously, it may endanger the patient's life. Thus, the need for improvement still exists.

SUMMARY OF THE INVENTION

It is therefore one object of the invention to provide a three-dimensional positioning device for minimally invasive surgery comprising: a base, two angle adjustable assemblies, an arc, a sliding assembly, a first positioning assembly, a second positioning assembly and a third positioning assembly. The base includes two first frames and two second frames. Two ends of each second frame are connected to the first frames respectively. Each first frame has a pivotal member. The angle adjustable assemblies are pivotably connected to the pivotal member of the first frame respectively.

The arc includes a hollow track member. The angle adjustable assemblies are connected to two ends of the arc. The sliding assembly is mounted on the track member of the arc according to a predetermined position of a nidus. The first positioning assembly is mounted on the second frame according to the predetermined position of the nidus. The second positioning assembly is mounted on the first positioning assembly. The third positioning assembly is mounted on the second positioning assembly.

In a first aspect of the invention, the first frames are parallel with each other.

In a second aspect of the invention, the second frames are parallel with each other.

In a third aspect of the invention, the first frame is perpendicular to the second frame.

In a fourth aspect of the invention, each pivotal member further comprises a scale.

In a fifth aspect of the invention, the arc further comprises two indicators disposed on the ends of the arc and being adjacent to and above the angle adjustable assemblies.

In a sixth aspect of the invention, the sliding assembly further comprises a positioning member, a clamping member, a connecting member and a clamping plate. The clamping member is threadedly connected to the connecting member through the clamping plate and the hollow track member. The clamping member clamps the clamping plate and the hollow track member to be fixedly mounted on the arc.

In a seventh aspect of the invention, the third positioning assembly further comprises a cauterizing needle and a threaded transmission shaft connected to the cauterizing needle. The threaded transmission shaft drives the cauterizing needle to move.

In an eighth aspect of the invention, the first positioning assembly further comprises a fixed member having a first groove, a first threaded shaft, a first transmission member having a second groove, a second threaded shaft and a second transmission shaft. The fixed member is adjustably mounted on the second frames. The first threaded shaft drives the first transmission member to move, and the second threaded shaft drives the second transmission member to move.

In a ninth aspect of the invention, the second positioning assembly further comprises an adjustment base having a curve member, a sliding member, a sliding base, two first clamping components and two second clamping components. The first clamping components are mounted through the sliding base. The first clamping components push the second clamping components to press the sliding member and the curve member. The sliding base is mounted fixedly on the curve member.

In a tenth aspect of the invention, each angle adjustable assembly comprises a rotatable member having two pressing parts, a cover having two cover grooves, two springs, two clipping members and two pressing members. The rotatable member is mounted on the arc. The cover contains the rotatable member, the springs, the clipping members and the pressing members. Each spring is mounted between the pressing part and the clipping member. Each pressing member is respectively mounted on each clipping member.

Each pressing member is disposed and limited in each cover groove. Pressing the pressing members rotates and positions the arc.

By utilizing the invention, the following advantages are obtained. First, the present invention provides a three-dimensional positioning device for minimally invasive surgery. The present invention can effectively improve the precision and operation more precisely in minimally invasive surgery to increase surgery success rate. Second, the present invention provides less moving directions for adjusting. Therefore, calculating of the positioning parameters is simpler and more convenient. The present invention is easy to operate, is a simple mechanism, is easy to manufacture, and is small and light. Thus, the present invention combines many advantages compared to the conventional positioning device.

The invention will become more obvious from the following description when taken in connection with the accompanying drawings.

DETAILED DESCRIPTION OF THE INVENTION

Figure 1:
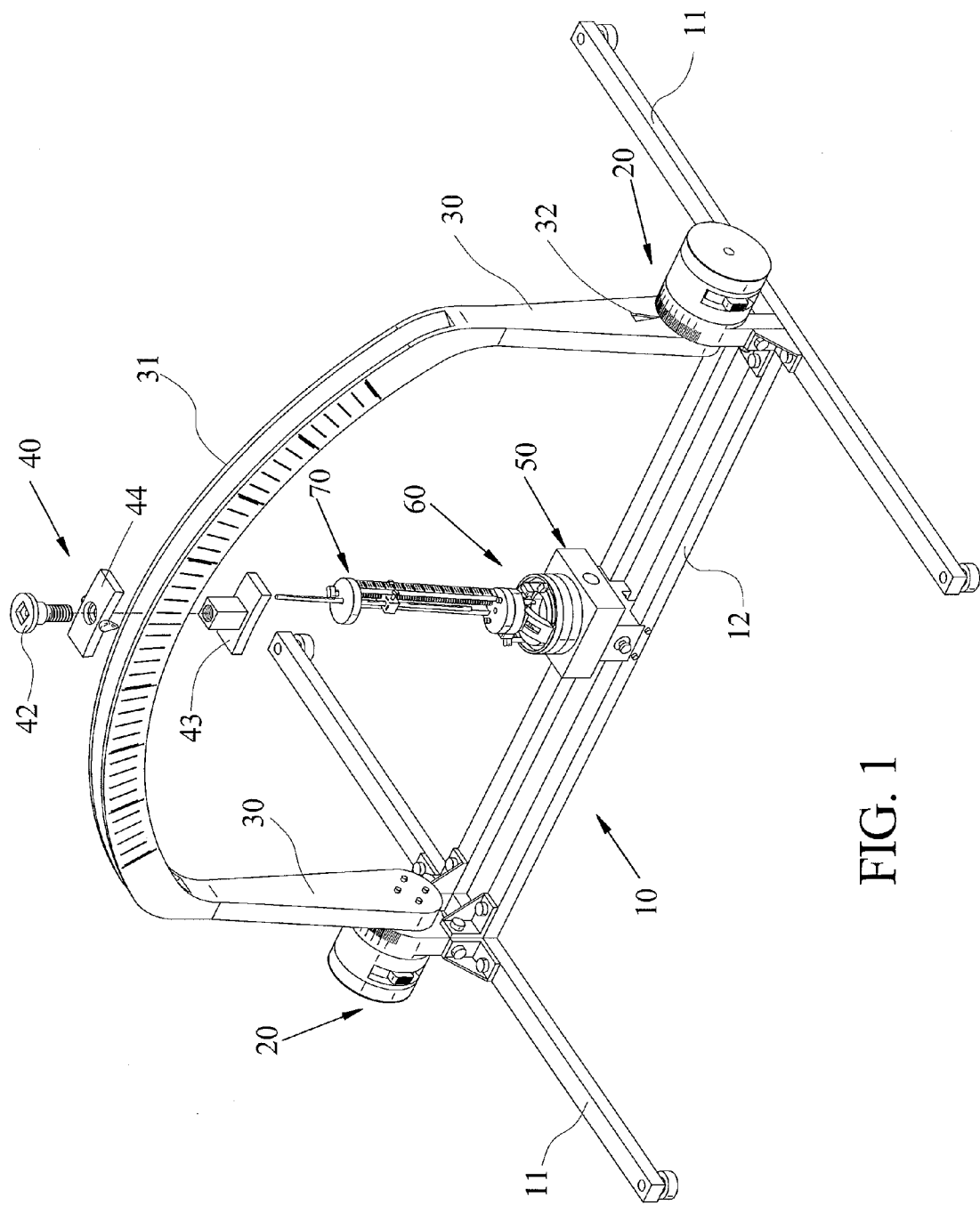
FIG. 1 is a perspective view to show the three-dimensional positioning device for minimally invasive neurosurgery of the invention.

Referring to FIGS. 1 to 4, a three-dimensional positioning device for minimally invasive surgery, e.g., neurosurgery, comprising: a base 10, two angle adjustable assemblies 20, an arc 30, a sliding assembly 40, a first positioning assembly 50, a second positioning assembly 60 and a third positioning assembly 70. The base 10 includes two first frames 11 and two second frames 12. Two ends of each second frame 12 are connected to the first frames 11 respectively. Each first frame 11 has a pivotal member 111. The angle adjustable assemblies 20 are pivotably connected to the pivotal member 111 of the first frame 11 respectively.

The arc 30 includes a hollow track member 31. The angle adjustable assemblies 20 are connected to two ends of the arc 30. The sliding assembly 40 is mounted on the hollow track member 31 of the arc 30 according to a predetermined position of a nidus. The first positioning assembly 50 is mounted on the second frames 12 according to the predetermined position of the nidus. The second positioning assembly 60 is mounted on the first positioning assembly 50. The third positioning assembly 70 is mounted on the second positioning assembly 60.

Preferably, the first frames 11 are parallel with each other.

Preferably, the second frames 12 are parallel with each other.

Preferably, the first frames 11 are perpendicular to the second frames 12.

Preferably, each pivotal member 111 further comprises a scale.

Preferably, the arc 30 further comprises two indicators 32 disposed on the ends of the arc 30 and adjacent to and above the angle adjustable assemblies 20.

Preferably, the sliding assembly 40 further comprises a positioning member 41, a clamping member 42, a connecting member 43, a clamping plate 44, and a guide 45 with a circular base. The clamping member 42 is threadedly connected to the connecting member 43 through the clamping plate 44 and the hollow track member 31. The clamping member 42 clamps the clamping plate 44 and the hollow track member 31 to be fixedly mounted on the arc 30.

Preferably, the third positioning assembly 70 further comprises a cauterizing needle 71 and a threaded transmission shaft 72 connected to the cauterizing needle 71. The threaded transmission shaft 72 can drive the cauterizing needle 71 to move.

Preferably, the first positioning assembly 50 further comprises a fixed member 51 having a first groove 511, a first threaded shaft 52, a first transmission member 53 having a second groove 531, a second threaded shaft 54 and a second transmission shaft 55. The fixed member 51 is adjustably mounted on the second frames 12. The first threaded shaft 52 can drive the first transmission member 53 to move, and the second threaded shaft 54 can drive the second transmission member 55 to move.

Preferably, the second positioning assembly 60 further comprises an adjustment base 61 having a curve member 611, a sliding member 62, a sliding base 63, two first clamping components 65 and two second clamping components 64. The first clamping components 65 are mounted through the sliding base 63. The first clamping components 65 push the second clamping components 64 to press the sliding member 62 and the curve member 611. The sliding base 63 is mounted fixedly on the curve member 611.

Preferably, each angle adjustable assembly 20 comprises a rotatable member 21 having two pressing parts 211, a cover 22 having two cover grooves 221, two springs 23, two clipping members 24 and two pressing members 25. The rotatable member 21 is mounted on the arc 30. The cover 22 contains the rotatable member 21, the springs 23, the clipping members 24 and the pressing members 25. Each spring 23 is mounted between the pressing part 211 and the clipping member 24. Each pressing member 25 is respectively mounted on each clipping member 24. Each pressing member 25 is disposed and limited in each cover groove 221. Pressing the pressing members 25 rotates and positions the arc 30.

Figure 4:
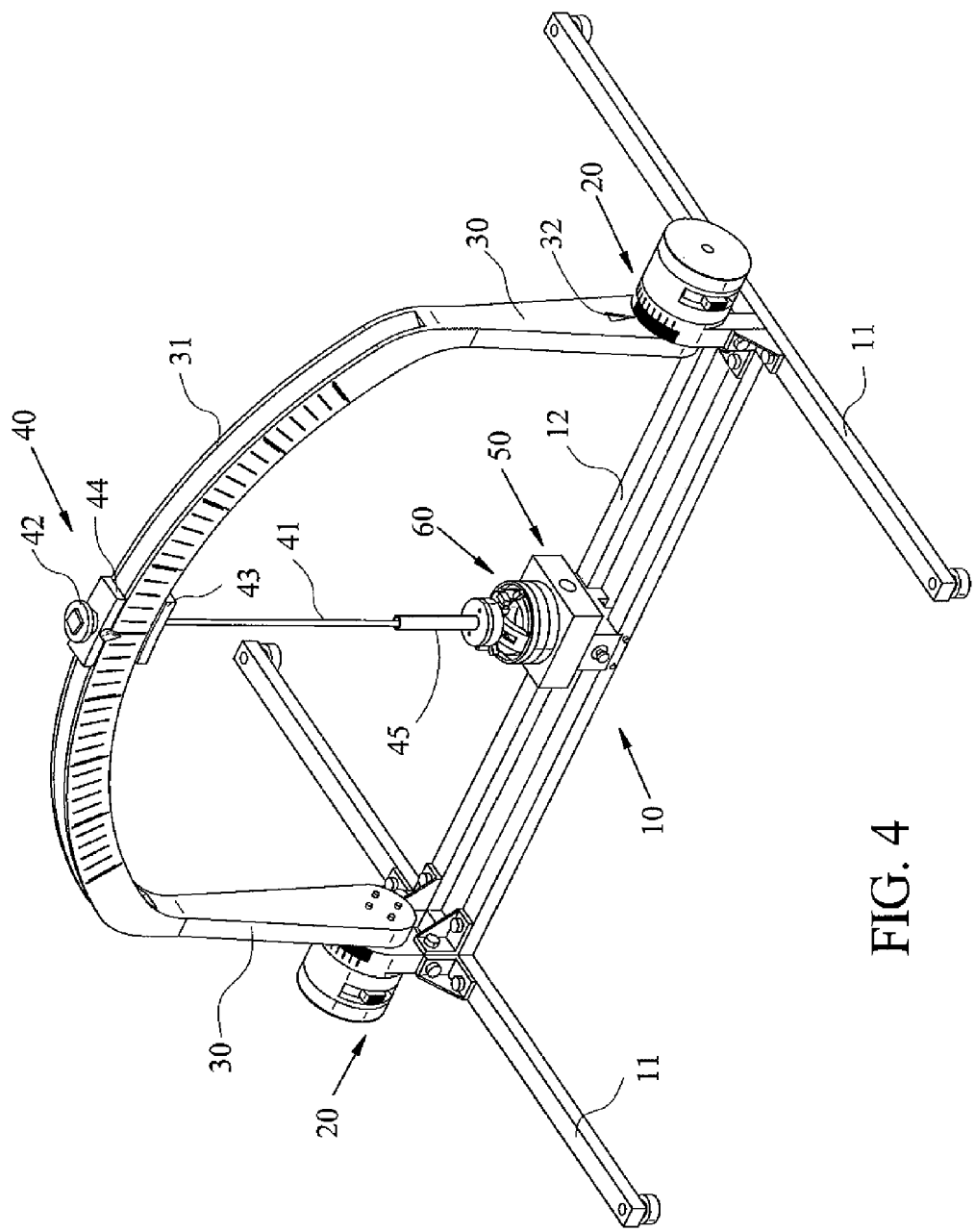
FIG. 4 is another perspective view to show how to adjust the three-dimensional positioning device of the invention.
Figure 5:
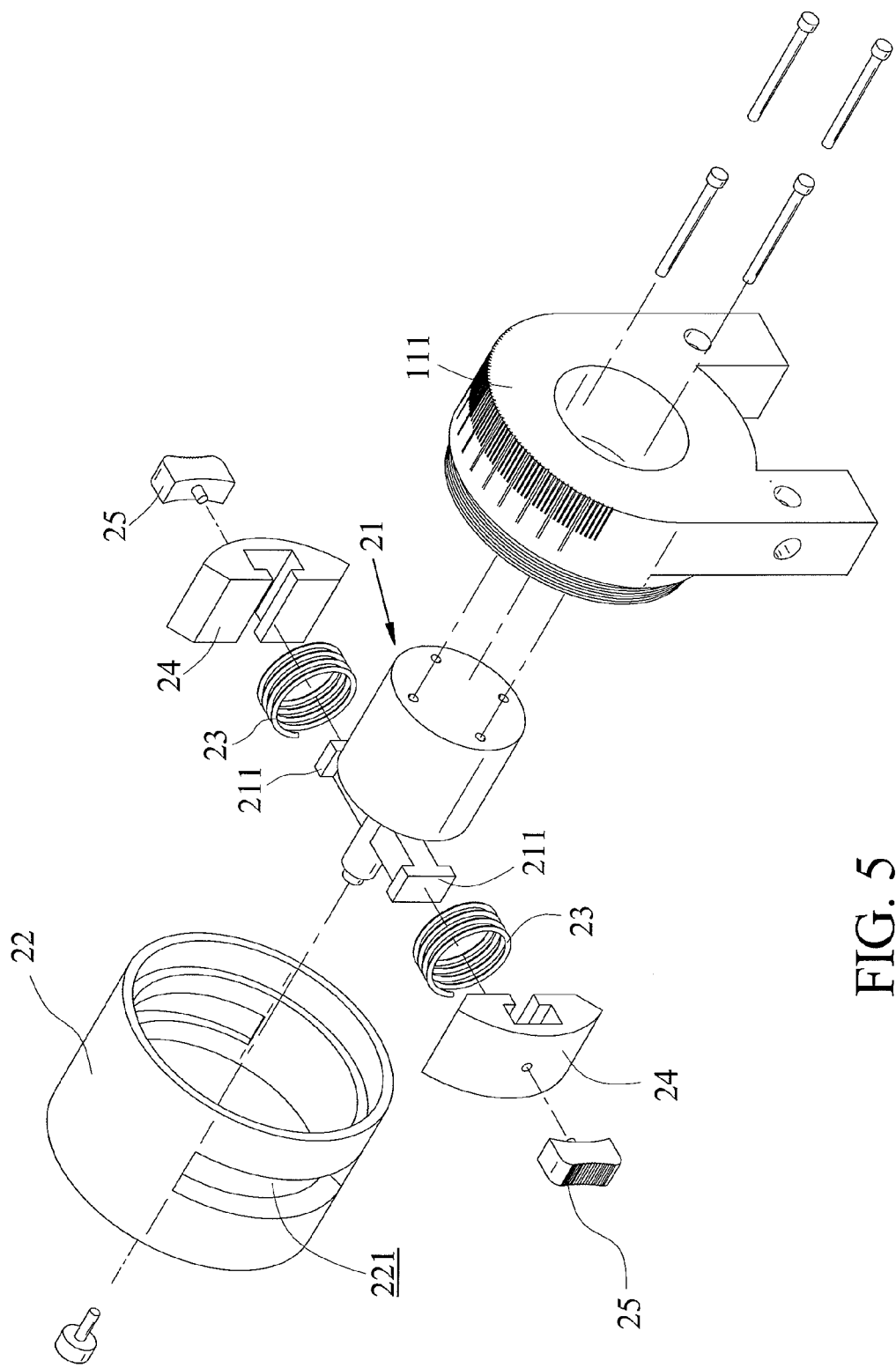
FIG. 5 is a partially exploded view to show the three-dimensional positioning device of the invention.
Figure 6:
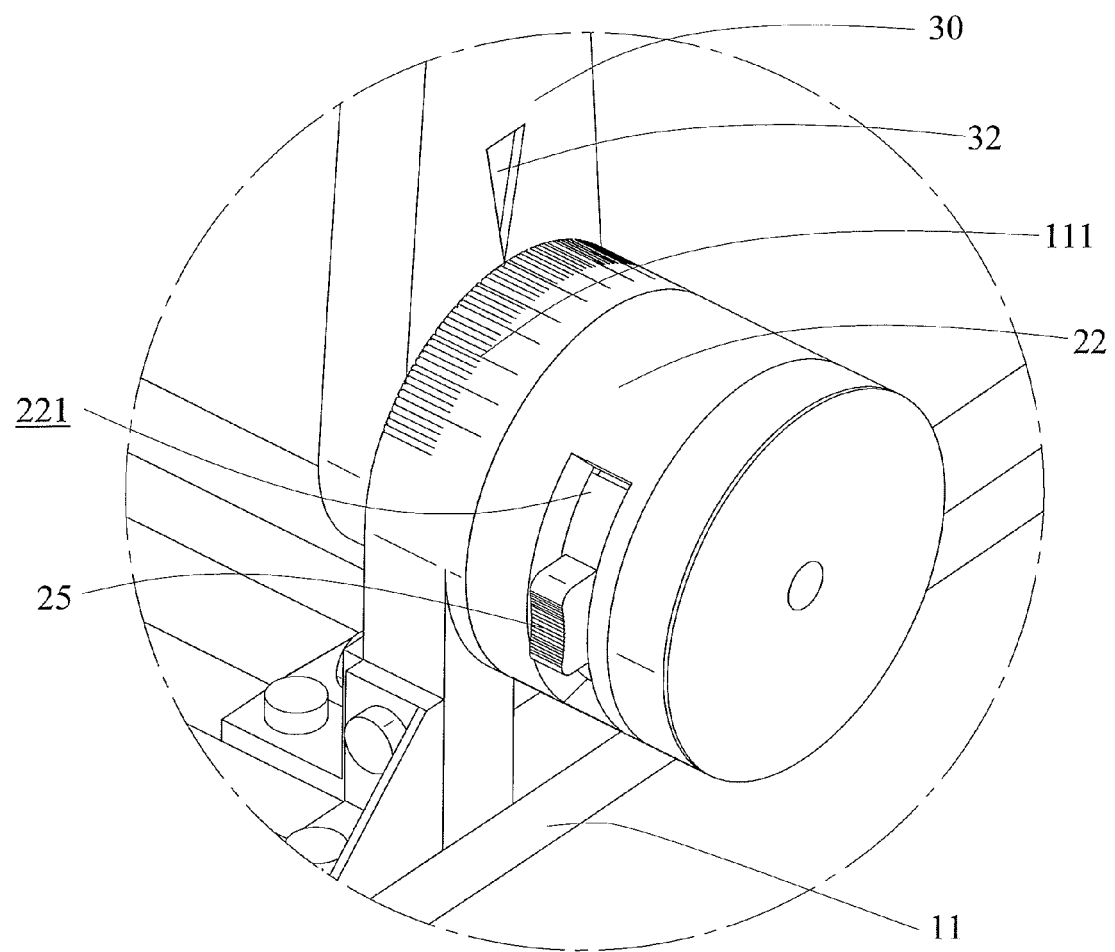
FIG. 6 is a partially exploded and enlarged view to show the three-dimensional positioning device of the invention.
Figure 7:
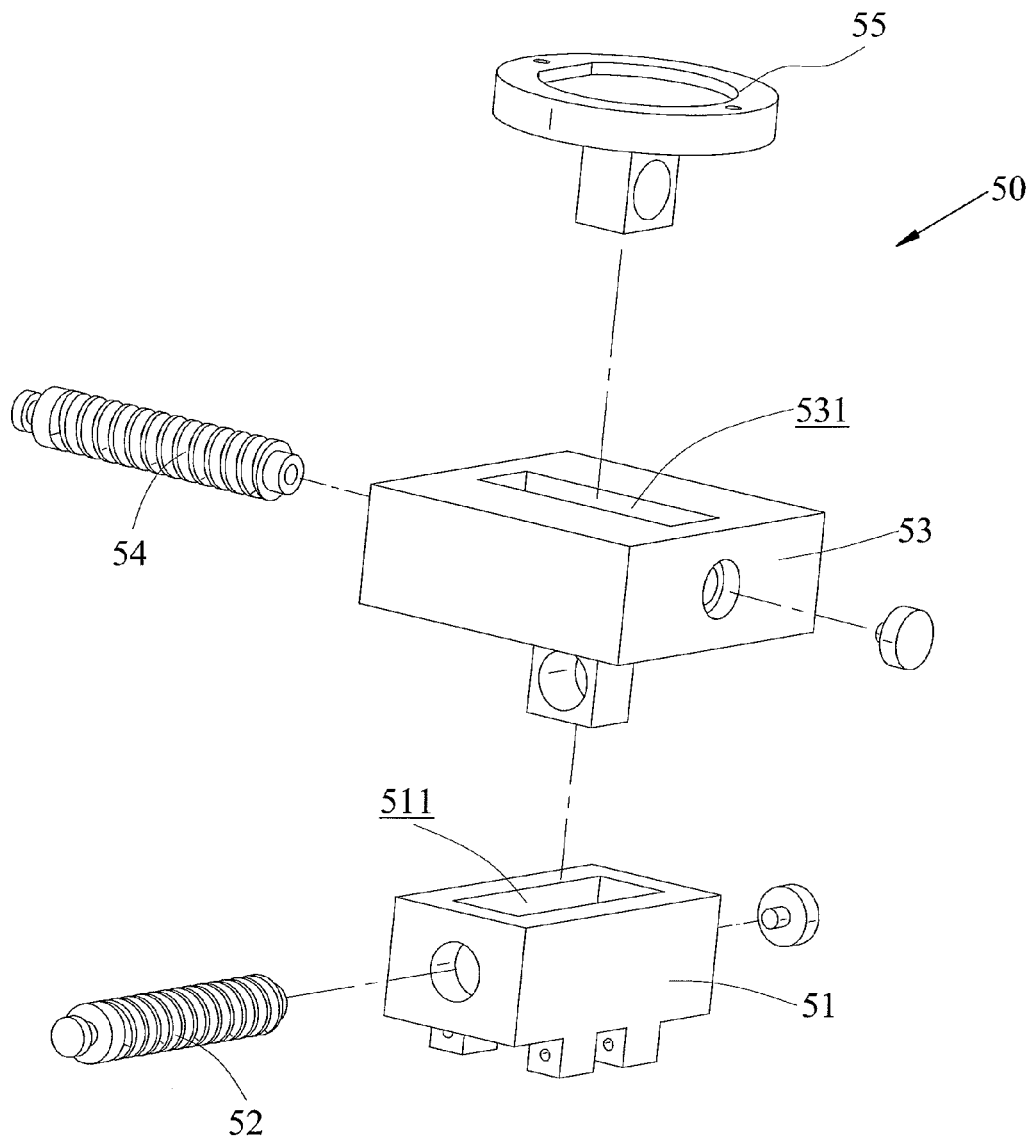
FIG. 7 is another partially exploded view to show the three-dimensional positioning device of the invention.
Figure 8:
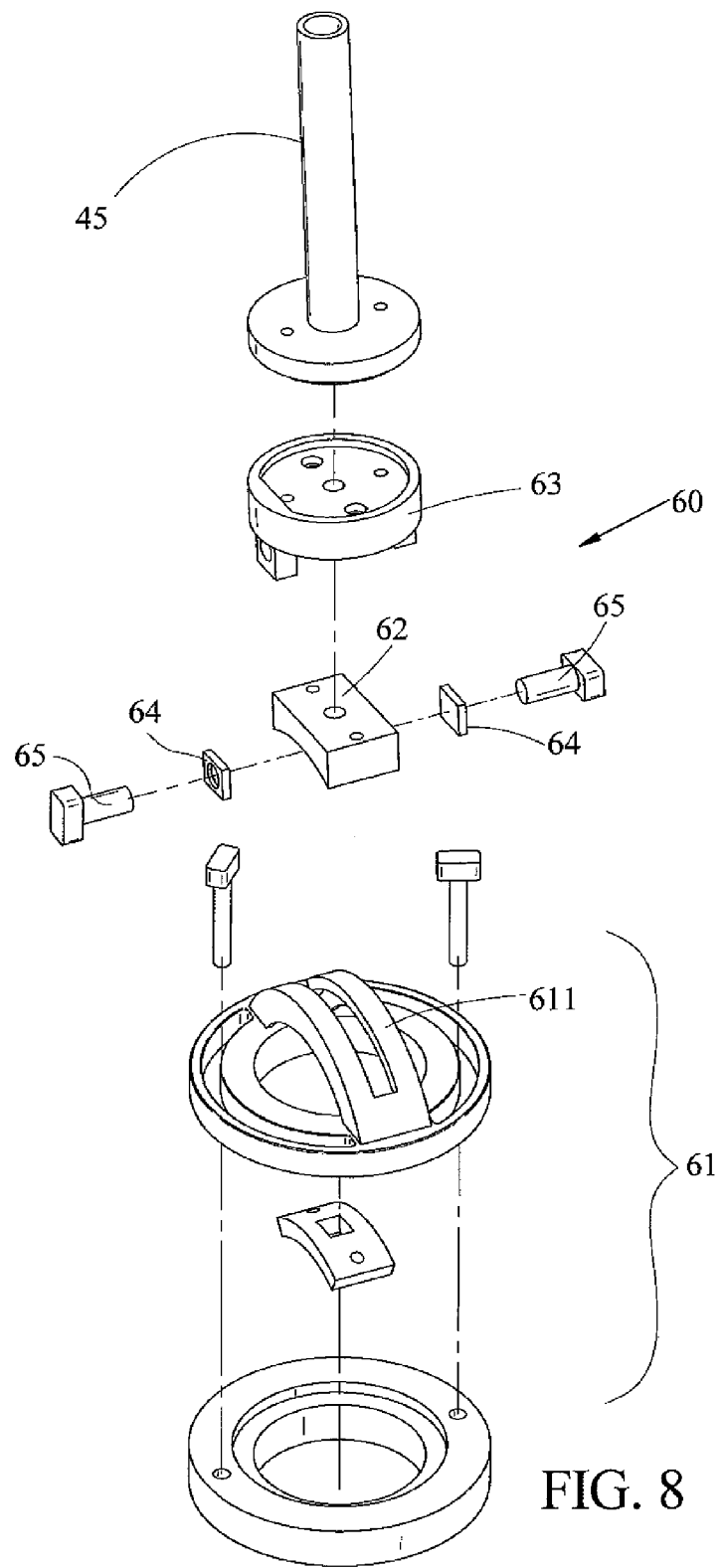
FIG. 8 is another partially exploded view to show the three-dimensional positioning device of the invention.
Figure 9:
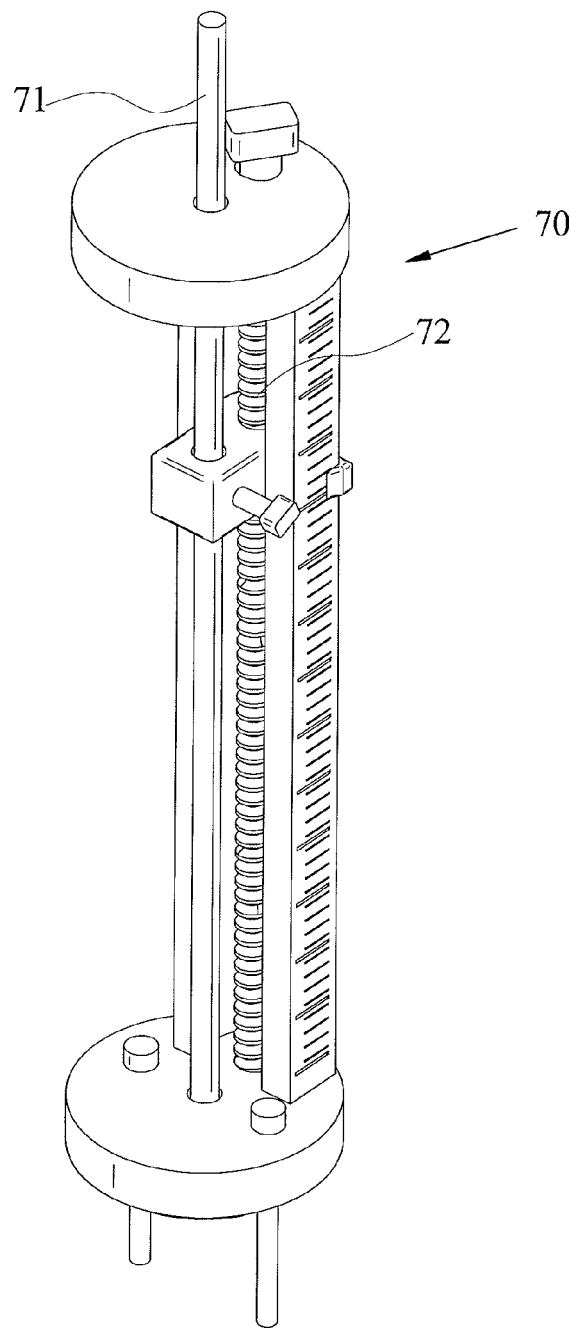
FIG. 9 is a partially perspective view to show the three-dimensional positioning device of the invention.
Figure 10:
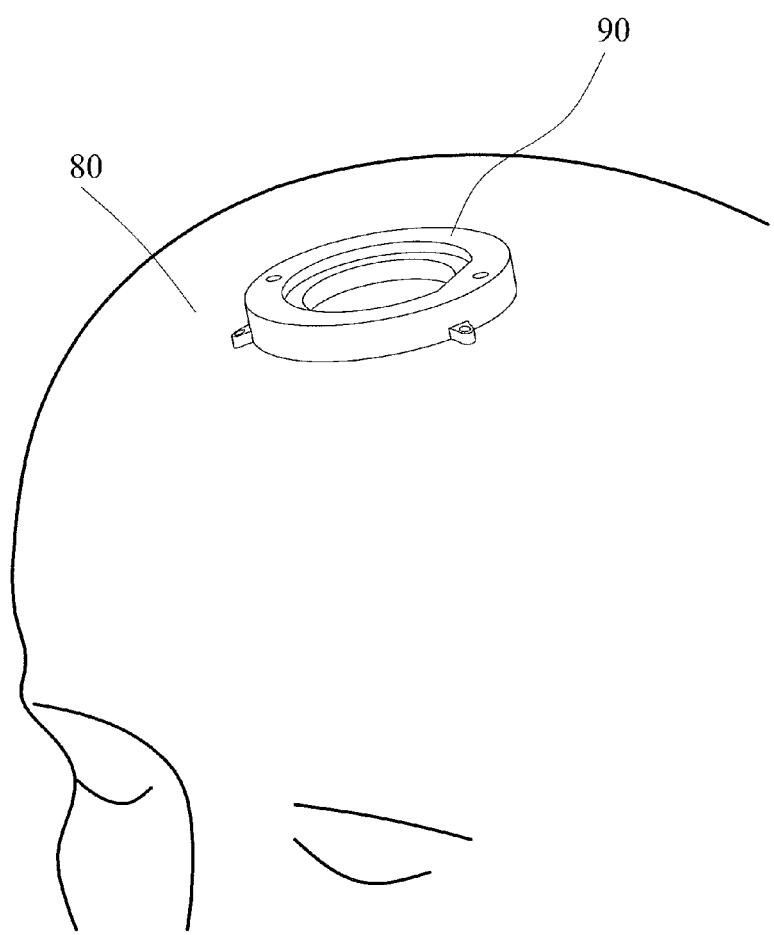
FIG. 10 is a partially perspective view to show a patient before a third positioning assembly mounting on the patient.
Figure 11:
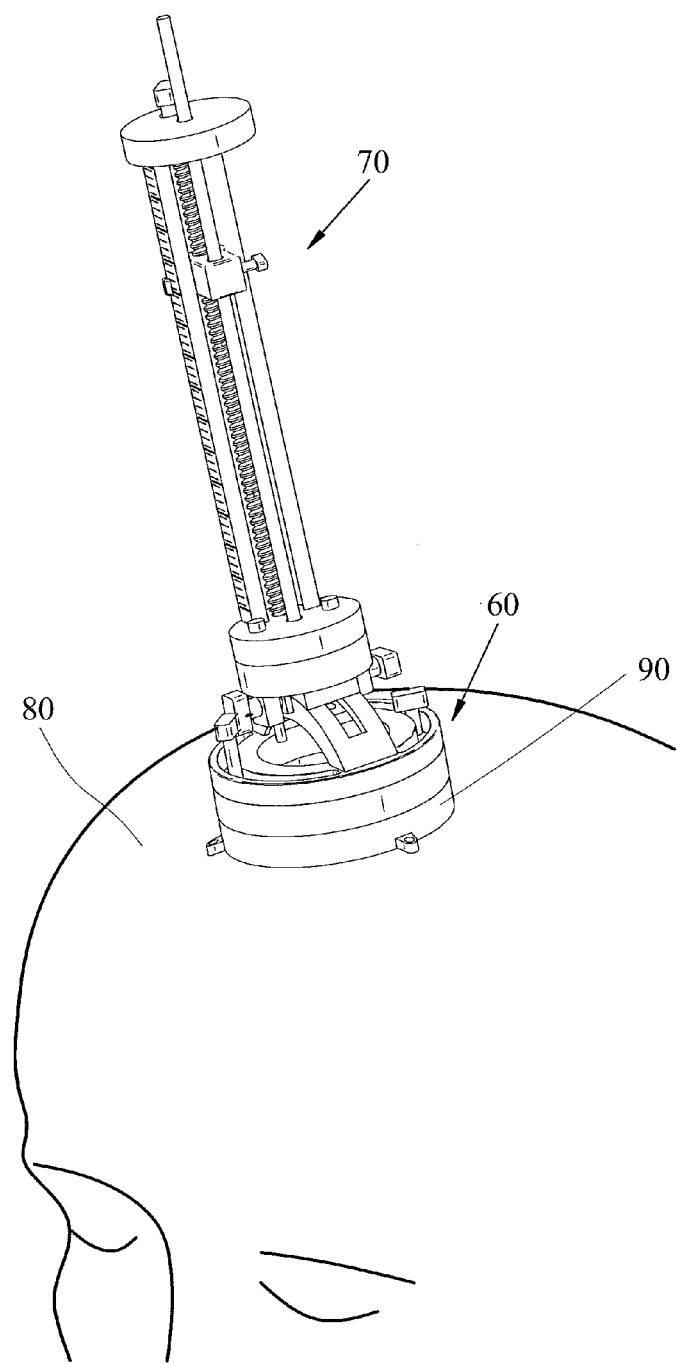
FIG. 11 is a partially perspective view to show a third positioning assembly of the invention mounted on the patient.
Figure 12:
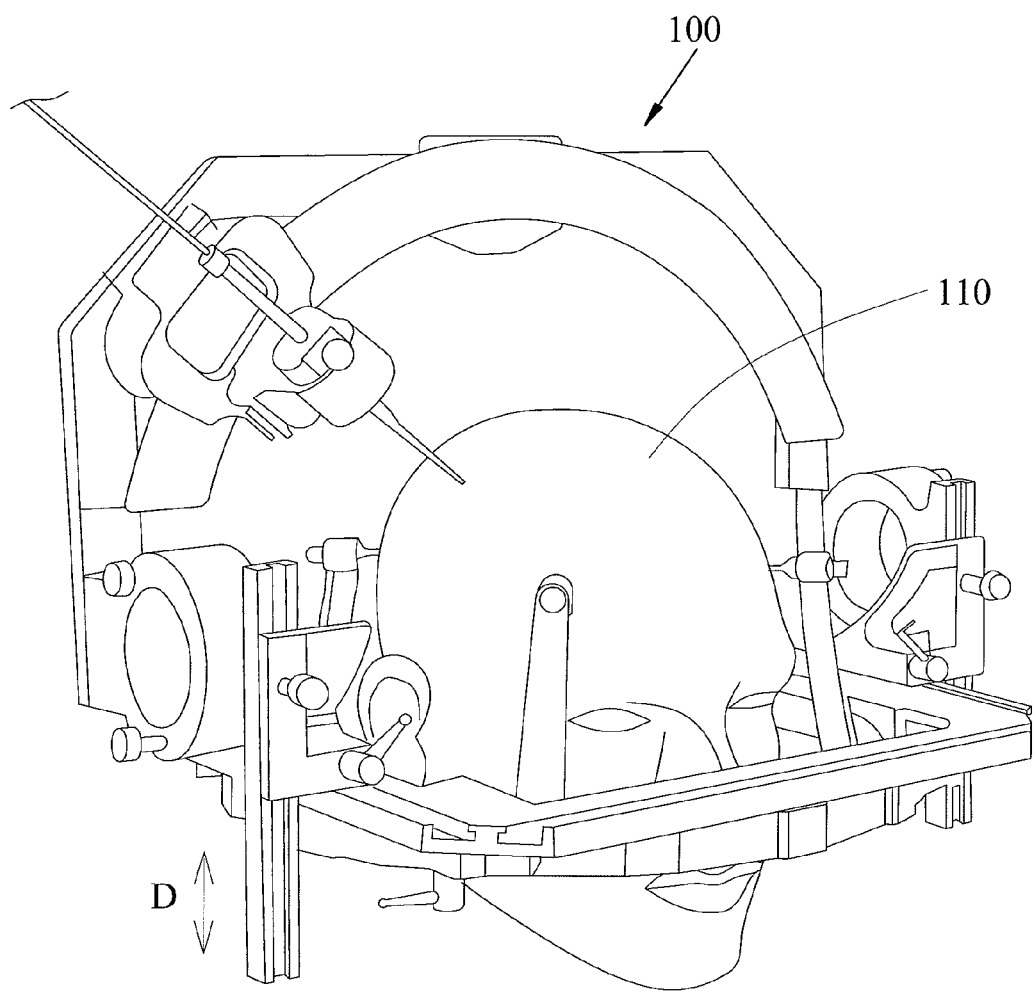
FIG. 12 is a perspective view to show a conventional three-dimensional positioning device.

Referring to FIG. 4, while adjusting the angle or direction, the positioning member 41 has to insert into the second positioning assembly 60. The guide 45 helps guide the positioning member 41 into the second positioning member 60. Therefore, the sliding assembly 40 is able to drive the second positioning assembly 60 to be positioned.

Figure 2:
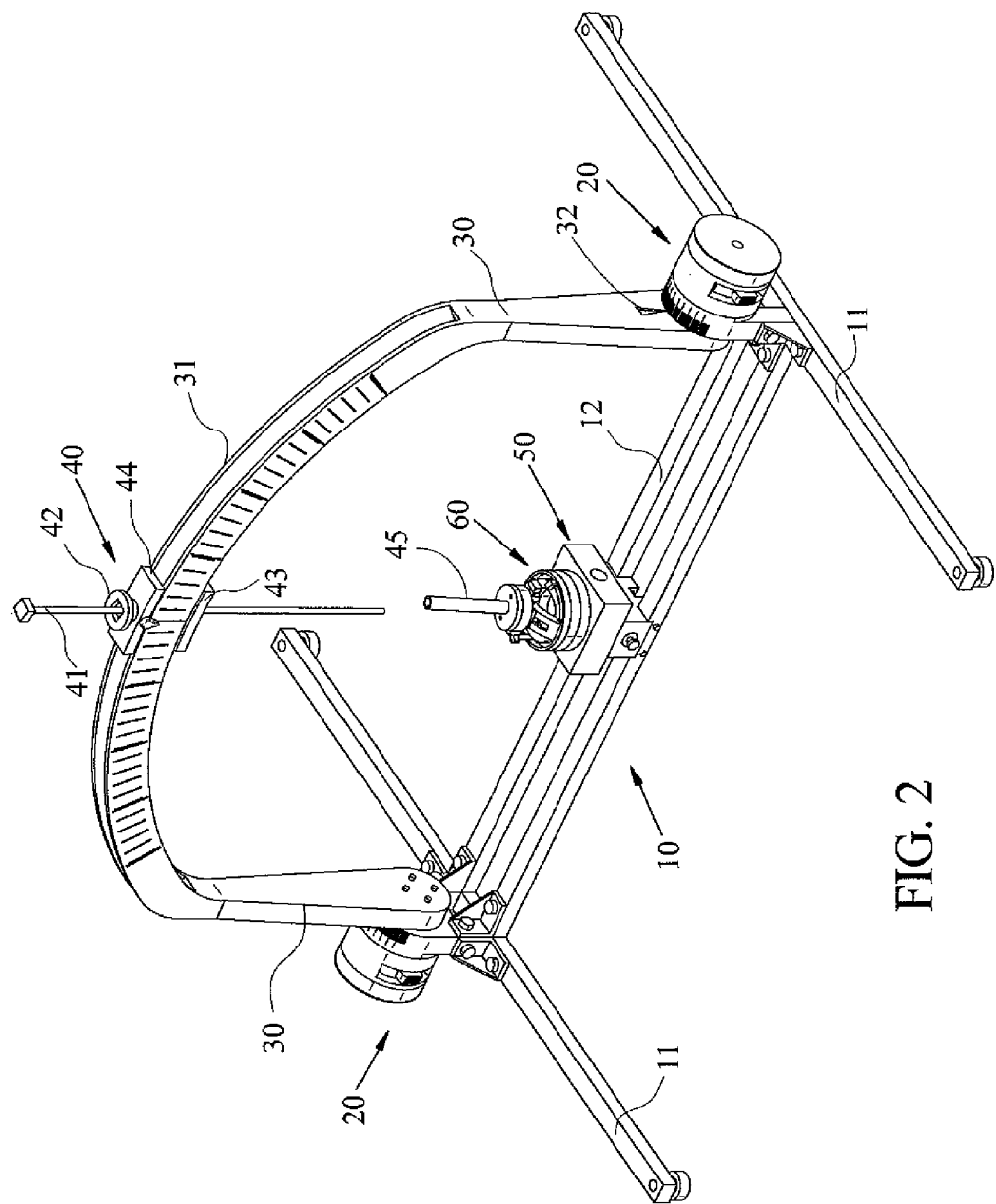
FIG. 2 is another perspective view to show the three-dimensional positioning device for minimally invasive neurosurgery of the invention.

The present invention in use is a mechanism as shown in FIG. 2. After positioning, the mechanism is fastened, and the positioning member 41 is removed to assemble as shown in FIG. 1. Then, the second positioning assembly 60 and the third positioning assembly 70 are mounted on a circular frame 90 mounted on the skull of the patient 80 for operating.

Figure 3:
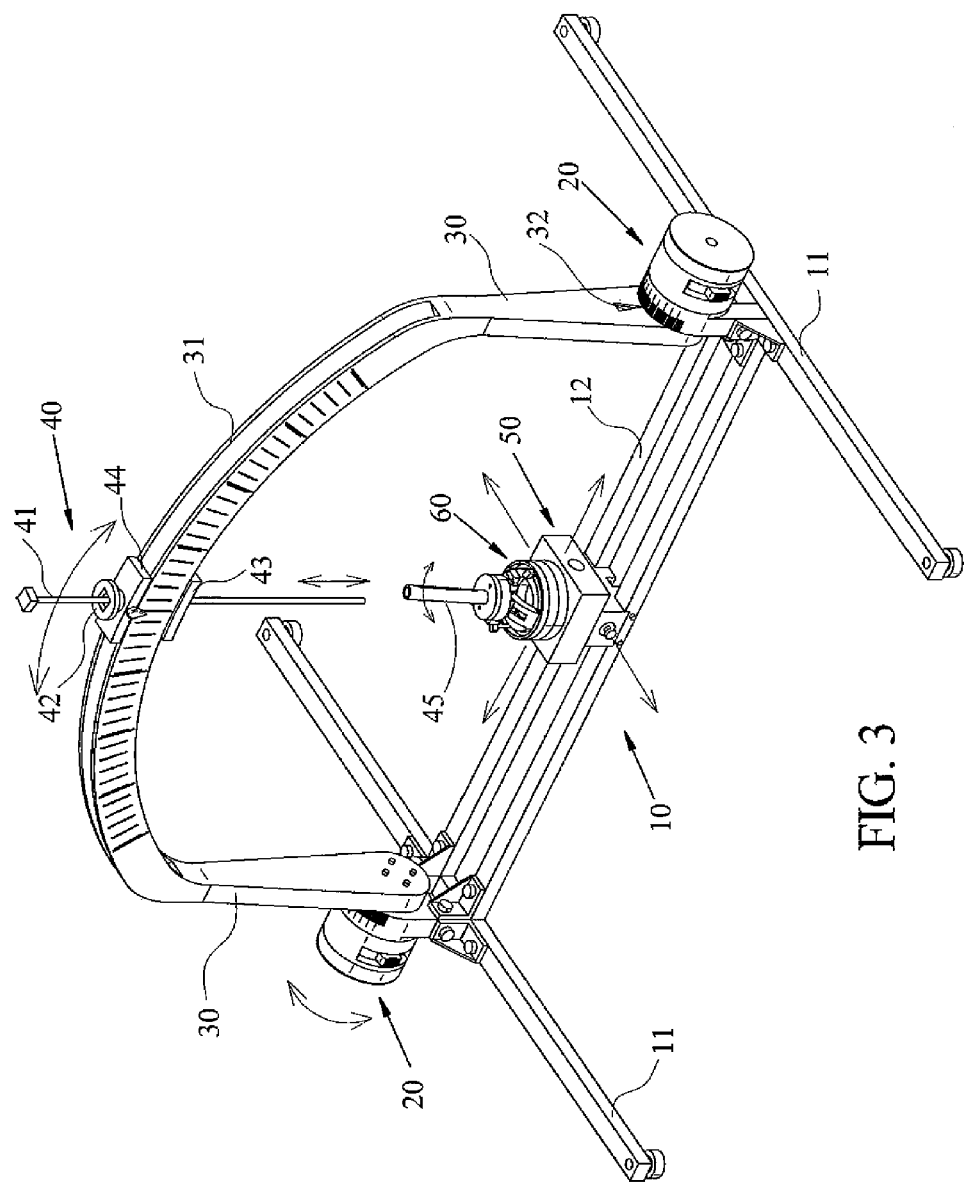
FIG. 3 is a perspective view to show how to adjust the three-dimensional positioning device of the invention.

Moreover, referring to FIG. 3, it is a perspective view showing how to adjust the three-dimensional positioning device of the invention. The present invention has less adjustment directions. Therefore, the present invention is with a simpler structure, has better precision and is easy to operate.

By utilizing the invention, the following advantages are obtained. First, the present invention provides a three-dimensional positioning device for minimally invasive surgery. The present invention can effectively improve the precision and operation more precisely in the minimally invasive surgery to increase surgery success rate. Second, the present invention provides less moving directions for adjusting. Therefore, calculating of the positioning parameters is simpler and more convenient. The present invention is easy to operate, has a simple mechanism, is easy to manufacture, and is small and light. Thus, the present invention combines many advantages compared to the conventional positioning device.

While the invention herein disclosed has been described by means of specific embodiments, numerous modifications and variations could be made thereto by those skilled in the art without departing from the scope and spirit of the invention set forth in the claims.

The invention claimed is:

1. A three-dimensional positioning device for minimally invasive surgery comprising:

a base including two first frames and two second frames, with two ends of each of the two second frames connected to the first frames respectively, with each of the two first frames having a pivotal member;

two angle adjustable assemblies pivotably connected to the pivotal members of the first frames respectively, wherein each of the two angle adjustable assemblies comprises a rotatable member having two pressing parts, a cover having two cover grooves, two springs, two clipping members, and two pressing members; wherein the cover contains the rotatable member, the two springs, the two clipping members, and the two pressing members, wherein each spring is mounted between one of the two pressing parts and one of the two clipping members, wherein each pressing member is mounted on a respective clipping member;

an arc including a hollow track member and having two ends connected to the two angle adjustable assemblies respectively, wherein the two rotatable members are mounted on the arc, wherein each pressing member is disposed and limited in a respective cover groove, and wherein the two pressing members are pressed to rotate and position the arc;

a sliding assembly mounted on the track member of the arc based on a predetermined position of a nidus;

a first positioning assembly mounted on the second frame based on the predetermined position of the nidus;

a second positioning assembly mounted on the first positioning assembly; and a third positioning assembly mounted on the second positioning assembly.

2. The device of claim 1, wherein the first frames are parallel with each other.

3. The device of claim 1, wherein the second frames are parallel with each other.

4. The device of claim 1, wherein the first frame is perpendicular to the second frame.

5. The device of claim 1, wherein each pivotal member of the two first frames further comprises a scale.

6. The device of claim 1, wherein the arc further comprises two indicators disposed on the two ends of the arc and adjacent to and above the two angle adjustable assemblies.

7. The device of claim 1, wherein the sliding assembly further comprises a positioning member, a clamping member, a connecting member, and a clamping plate; wherein the clamping member is threadedly connected to the connecting member through the clamping plate and the hollow track member, and wherein the clamping member clamps the clamping plate and the hollow track member to be fixedly mounted on the arc.

8. The device of claim 1, wherein the third positioning assembly further comprises a cauterizing needle and a threaded transmission shaft connected to the cauterizing needle; and wherein the threaded transmission shaft drives the cauterizing needle to move.

9. The device of claim 1, wherein the first positioning assembly further comprises a fixed member having a first groove, a first threaded shaft, a first transmission member having a second groove, a second threaded shaft, and a second transmission shaft; wherein the fixed member is adjustably mounted on the second frames, and wherein the first threaded shaft drives the first transmission member to move and the second threaded shaft drives the second transmission member to move.

10. the device of claim 1, wherein the second positioning assembly further comprises an adjustment base having a curve member, a sliding member, a sliding base, two first clamping components, and two second clamping components; wherein the first clamping components are mounted through the sliding base, wherein the first clamping components push the second clamping components to press the sliding member and the curve member, and wherein the sliding base is mounted fixedly on the curve member.

* * * * *